United States Patent [19]

Manning et al.

[11] 3,965,044

[45] June 22, 1976

[54] METHOD OF METAL CHROMITE PREPARATION

[75] Inventors: Harold E. Manning; Michael C. Ellis, both of Houston, Tex.

[73] Assignee: Petro-Tex Chemical Corporation, Houston, Tex.

[22] Filed: Aug. 1, 1974

[21] Appl. No.: 493,500

[52] U.S. Cl............................. 252/465; 252/467; 252/468; 252/470
[51] Int. Cl.² ................... B01J 21/04; B01J 23/16; B01J 23/84
[58] Field of Search .......... 252/465, 467, 468, 470; 423/595

[56] References Cited
UNITED STATES PATENTS

| | | | |
|---|---|---|---|
| 1,934,795 | 11/1933 | Frazer | 252/470 |
| 2,205,141 | 6/1940 | Heard | 252/470 X |
| 3,781,376 | 12/1973 | Manning | 260/683.3 |

*Primary Examiner*—W. J. Shine
*Attorney, Agent, or Firm*—N. Elton Dry; Kenneth H. Johnson

[57] ABSTRACT

Metal chromite dehydrogenation catalysts are made by preparing an aqueous solution of $CrO_3$, dissolving a second metal compound, such as MgO, therein adding a reducing agent, precipitating a substantially insoluble oxide of Mg and Cr, recovering the precipitate and calcining it to produce a Mg chromite dehydrogenation catalyst.

14 Claims, No Drawings

METHOD OF METAL CHROMITE PREPARATION

BACKGROUND OF THE INVENTION

This invention relates to method of preparing metal chromite dehydrogenation catalysts.

Recently it has been found that magnesium chromites are excellent dehydrogenation catalysts (U.S. Pat. No. 3,781,376). Prior to this discovery, chromia-alumina catalysts had been considered far superior to other materials for dehydrogenations. The dehydrogenation process is a cyclic process in which gaseous hydrocarbons such as butane, isobutane, isopentane or ethylbenzene are dehydrogenated over a suitable catalyst to produce butenes and butadiene, isopentene and isoprene and styrene, respectively. After each dehydrogenation cycle there is a catalyst regeneration cycle in which the accumulated coke is burned off by passing molecular oxygen through the catalyst followed by another dehydrogenation cycle and so on.

The chromia-alumina catalysts are prepared by treating activated alumina with a solution of chromic acid, draining off the excess acid from the alumina, drying and heat treating at about 1400°F. Commercial chromia-alumina dehydrogenation catalysts normally contain about 20% chromium oxide. Preparative methods are shown, for example, in U.S. Pat. Nos. 2,399,678 and 2,419,997.

Metal chromite formation can be accomplished by reacting an active compound of chromium with an active compound of magnesium and the other designated metals. By active compound is meant a compound which is reactive under the conditions to form the chromite. Starting compounds of chromium, magnesium or the other metals may be such as the nitrates, hydroxides, hydrates, oxalates, carbonates, acetates, formates, halides, oxides, etc.

The magnesium chromite can be prepared by precipitation, dry or wet milling or mixing, by precipitation of one of the ingredients in the presence of the other, coprecipitation and impregnation of one or more of the solid ingredients with aqueous or non-aqueous solutions of salts of the ingredients. The coprecipitation of the chromite precursors is a preferred method of obtaining intimate mixing thereof; however, prior methods of obtaining coprecipitate have had serious drawbacks which had been contraindicative of their use.

The prior method of coprecipitation consisted of dissolving soluble compounds of a metal, such as magnesium, and chromium in an aqueous solution and precipitating an insoluble mixture of hydroxides by using ammonium hydroxide and sodium or potassium hydroxide. Generally, Na and K hydroxides were not employed since residual alkali metal tends to deactivate the resultant chromite. Ammonium hydroxide does not have this defect and was usually employed for obtaining coprecipitates of magnesium and chromium compounds in the past; however, the ammonium salts in the supernatant liquid tended to resolublize the precipitates.

It is a feature of the present invention that a method of obtaining coprecipitation of metal and chromium components of the chromite has been devised which does not require hydroxide precipitates. It is a particular feature of the present invention that a precipitate is recovered which produces a high-quality magnesium chromite dehydrogenation catalyst. An advantage of the present invention is a very simple procedure which is easily driven to completion and the products produced therein do not require extensive purification to employ them to prepare the chromite dehydrogenation catalyst. These and other features and advantages of the present invention will be clearer from the following discussion and description.

SUMMARY OF THE INVENTION

Briefly stated it has been found that metal chromites may be prepared by preparing an aqueous solution of a chromium (VI) compound and a soluble compound of a second metal, admixing this solution with an organic reducing agent, soluble in water, precipitating a substantially water insoluble compound of chromium and the second metal, and recovering the insoluble compound. Preferably the composition recovered as a precipitate is calcined to increase the catalytic activity.

DETAILED DESCRIPTION OF THE INVENTION

The catalysts of this invention contain a divalent metal, chromium (III), and oxygen which are chemically combined in such a manner as to form a definite and discrete inorganic chemical compound generally referred to in the literature as metal chromite. The chromite, like most other chromites, is isostructural to the mineral spinel (magnesium aluminate) and consequently can be said to have the spinel structure which is a face-centered cubic form.

The catalysts of the present invention are predominately chromites, that is, they contain more than 50% by weight of the chromite. Preferably the catalysts contain 75% or more chromites, i.e., 90% chromites. The chromites generally may be represented by the formula $MeCr_2O_4$ where Me is one or more divalent ions of Mg, Sr, Ba, Fe, Mn, Co, Ni, Cu, Zn, Cd, or Be preferably Mg. A portion of the magnesium can be replaced with other metals having an ionic radius approximately between about 0.5 and 1.1A, preferably between about 0.6 and 1.0A. In the case of such mixed chromites, Mg may be the predominant Me ion, comprising at least 50 atomic % of the Me ions present. In addition to Mg the Me may be one or more of the divalent ions of Ca, Sr, Ba, Fe, Mn, Co, Ni, Cu, Zn, Cd, or Be.

The metal chromites of the present invention exhibit a certain type of X-ray diffraction pattern. The peaks observed in the X-ray diffraction pattern may not have sharp peaks such as those found, e.g., in highly crystalline material of the same chemical composition, but can and do frequently exhibit relatively broad reflection peaks. The degree of sharpness of the reflection peak may be measured by the reflection peak band width at half height (W/h/2). In other words, the width of the reflection peak as measured at one-half of the distance to the top of the peak is the "band width at half height". The band width at half height is measured in units of °2 theta. Techniques for measuring the band widths are discussed, e.g., in Chapter 9 of Klug and Alexander, X-ray Diffraction Procedures, John Wiley and Son, N.Y., 1954. The observed band widths at half height of the preferred compositions of this invention are at least 0.12°2 theta and normally will be at least 0.16°2 theta. *

*The powder diffraction patterns may be made, e.g. with a Norelco constant potential diffraction unit type No. 12215/0, equipped with a wide range goniometer type No. 42273/0, copper tube type No. 32147, proportional counter type No. 57250/1; all coupled to the Norelco circuit panel type No. 12206/53. The copper K alpha radiation is supplied by operating the tube at a constant potential of 40 kilovolts and a current of 35 milliamperes. A nickel filter is used to remove K beta radiation. The detector voltage is 1600 volts and the pulse height analyzer is set to accept pulses with amplitudes between 10 and 30 volts only. Slits used are divergence 1°, receiving 0.006 inches and scatter 1°. Strip chart recordings for identification are made with a scanning speed of 1° per minute, time constant of 1 second and a full scale at $10^3$ counts per second. No correction is made for K $\alpha$ doublet or instrumental broadening of the band widths.

Coprecipitation is an excellent method of obtaining initmate mixing of chromite precursors, e.g., chromium trioxide and magnesium oxide. According to the present invention, a solution of the chromium (VI) and magnesium or other Me metals is prepared. The theoretical ratio of Cr/Mg in $MgCr_2O_4$ (stoichiometric) is 2/1. However, either compound may be present in an excess over the stoichiometric amount to an extent of about 10 mol % without substantial change in the character of the chromite catalyst produced.

Water soluble compounds of chromium and the other metals for use in the coprecipitation include chromium trioxide ($CrO_3$), chromyl nitrate ($CrO_2(NO_3)_2$, chromyl perchlorate ($CrO_2(ClO_4)_2$), chromyl acetate, magnesium acetate, magnesium chloride, magnesium chloride, magnesium bromide, magnesium carbonate, magnesium dichromate, magnesium chromate, magnesium benzoate, magnesium hydroxide, magnesium formate, magnesium nitrate, magnesium oxide, calcium chloride, barium hydroxide, copper chloride, cobalt chloride, cadium bromide, stronium formate, iron nitrate, nickel chloride, zinc chloride, and the like. Soluble compounds of the listed metals are well known and an extensive number thereof is set forth in the *Handbook of Chemistry and Physics*, 51st Edition 1970–1971, The Chemical Rubber Co., Cleveland, Ohio. p. B63 – B156, which is incorporated to the extent of showing said water soluble compounds.

Chromium (VI) forms a large number of oxygen compounds, which may be regarded as derived from Cr (VI) oxide. These include the oxy-halogen complexes and chromyl compounds, chromates, dichromates, trichromates, tetrachromates, and basic chromates. Any Cr (VI) compound that is sufficiently water soluble may be employed in present invention.

The concentration of each component is adjusted to produce the desired ratio of Me and Cr in the chromite. Chromium trioxide is reduced on a substantially stoichiometric basis to $Cr_2O_4$ =; however, the Me which is present as a soluble compound may not be converted on a stoichiometric basis, depending on the solubility of the Me compounds formed, and hence is generally employed in the solution in excess of the stoichiometric amount, unless it is desired to produce a catalyst with an excess of chromium. Generally, the soluble Me metal compound will be present in an amount of from 10 to 50 mol % excess of the stoichiometric amount based on $MeCr_2O_4$.

The present invention is thought to proceed in the following reaction:

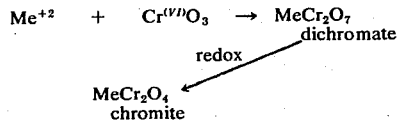

Particular preferred Me is Mg, Zn, or Co, and Mg is especially preferred as a chromite component for use as a dehydrogenation catalyst.

Any of the known organic reducing agents may be employed to reduce the chromium to the +3 state and hence produce insoluble $MeCr_2O_4$. For example, formaldehyde, paraformaldehyde, acetaldehyde, aryl alkanes, such as toluene, primary alcohols, secondary alcohols, water soluble polyhydric compounds including polyhydric alcohols, dipropylene glycol, diethylene glycol, trietthylene glycol, 1,3-butylene glycol, 2,2-dimethyl-1,e-propanediol and 2,2,4-trimethyl-1,3-pentanediol; triols, such as glycerol, 1,2,4-butanetriol, 2-hydroxymethyl-2-methyl-1,3-propanediol, 2-ethyl-2hydroxymethyl-3,3-propane diol, 1,2,6-hexanetriol; higher polyols and polyols such as erythritol, pentaerythritol, xylitol, sorbitol, perseitol, octitol, anhydroenneaheptitol, dipentaerythritol; tripentaerythritol; lower saccharides such as ribose, xylose, sorbose, glucose, heptulose (monosaccharides), polysaccharides such as lactose maltose, methylglucoside (disaccharides), raffinose, melezitose, (trisaccharides) and the like.

The reducing agent may be employed in a stoichiometric amount, but is generally employed in an excess of about 50 to 400 mol % based on the Cr (VI) to be reduced.

The redox reaction is exothermic; however, it has been found expedient to initiate the reaction by heating the reaction mixture after adding the reducing agent to a temperature of from about 75° to 100°C. The temperature of the reaction mixture should be maintained at a temperature in the range of about 90° to 100°C (at atmospheric pressure) in order to drive it to completion. The reaction is completed when there is no longer any precipitation or when heat is no longer being generated by the reaction.

The precipitate recovered comprises principally the insoluble metal chromite $MeCr_2O_4$, however, there may be some other insoluble materials produced, e.g., $Cr_2O_3$ or Me $(OH)_2$, however, these are generally minor or insubstantial components. Although a compound identifiable as a metal chromite is recovered, it has been found that an active dehydrogenation catalyst is prepared by calcining the recovered material at an elevated temperature e.g., 400°–1100° C (generally no greater than 1300°C) in a controlled atmosphere, as described below. A calcination temperature of 550°–900°C has been found particularly useful and temperature in the range of 600°–800°C have been found to produce excellent catalysts.

The activation of the chromite may be obtained by heating the chromite at an elevated temperature, in a controlled atmosphere, i.e., air, nitrogen, oxygen, a reducing atmosphere such as hydrogen, carbon monoxide, or the like, for a sufficient time, i.e., usually 5 minutes to 4 hours. Similarly, a degree of activation is achieved as the catalyst is employed in a dehydrogenation process, since the conditions of temperature and atmosphere as approximate preactivation.

Particularly preferred magnesium chromite is activated in an atmosphere containing less oxygen than normally contained in air, such as less than 15 or 20 mol percent oxygen. By thus causing the reaction to take place in an atmosphere deficient in oxygen, the metal portion of the chromite is less prone to be oxidized to a higher valence and an atmosphere absent any oxygen may be beneficial, such as an atmosphere of nitrogen or helium. The nature of a preferred atmosphere used to calcine or sinter the metal chromite is one in which the reactants and the metal chromites produced are essentially inert. Thus the atmosphere would be an essentially inert atmosphere rather than either an essentially oxidizing atmosphere or an essentially reducing reducingn atmosphere, although small quantities of non-inert gases, e.g., either or both of oxidizing or reducing gases, or other reactive gases, i.e., about up to 3 mol percent would be acceptable in the preferred embodiment. As defined herein an inert atmosphere comprises essentially nitrogen, helium, neon, argon, krypton, xenon, radon, and mixtures thereof.

A particularly preferred magnesium chromite is one such as described and claimed in U.S. Pat. No. 3,781,376 wherein the magnesium chromite contains aluminum therein; and the disclosure of that patent in regard thereto is incorporated herein. The preferred catalyst contains chromium, magnesium, aluminum and oxygen. The catalysts are characterized as magnesium chromites either in admixture with aluminum oxide or containing aluminum therein and can be considered as aluminum promoted magnesium chromites.

THe aluminum component of the catalyst may also be present as a constituent of the chromite, however, it is not necessary that the aluminum be a portion of the chromite and may be present in addition to the metal chromite in the form of aluminum oxide.

The aluminum component of the catalyst can be added prior to and/or after the calcination of the chromite. The aluminum component is conveniently added to the chromite as a soluble salt in a slurry with the chromite after which it is dried; then decomposed by heating to aluminum oxide. Alternatively insoluble aluminum oxide can be added to the magnesium chromite, preferably in a highly divided state.

The aluminum will be present in the catalyst in all forms in an atomic ratio of Al:Cr of 0.0004 to 1.2:1. For example, in terms of a soluble aluminum compound such as aluminum sulfate, added to the magnesium chromite this would represent from about 0.1 to 75 weight percent $Al_2(SO_4)_3 \cdot 16H_2O$ based on the total weight of the catalyst. A preferred range of Al:Cr atom ratio is 0.04 to 0.8:1. Generally the higher weight percentages of aluminum compound, i.e., 50 weight percent or more, are applied to the magnesium chromites having high surface areas, e.g., $50m^2$ per gram or more.

The active catalysts can be pelleted or applied to a suitable support, such as alumina, silica gel, silica-alumina, firebrick, kieselguhr, quartz, and the like. The catalyst is the active surface available for contact with the gaseous reactants.

The catalysts of this invention can be applied to the dehydrogenation of a wide variety of organic compounds, particularly parafin and olefin hydrocarbon compounds. Such compounds normally will contain from 2 to 20 carbon atoms, at least one

grouping, having a boiling point below about 350° C, and may contain other elements, in addition to carbon and hydrogen such as oxygen, halogens, nitrogen and sulfur. Preferred are compounds having 2 to 12 carbon atoms, and especially preferred are compounds of 3 to 8 carbon atoms.

Representative materials are dehydrogenated by the novel process of this invention include n-butane, ethyl toluene, alkyl chlorobenzenes, ethyl napthalene, isobutyronitrile, propyl chloride, isobutyl chloride, ethyl fluoride, ethyl bromide, n-pentyl iodide, ethyl dichloride, 1,3-dichlorobutane, 1,4-dichlorobutane, the chlorofluoroethanes, methyl pentane, methylethyl ketone, diethyl ketone, n-butyl alcohol, methyl propionate, isobutane, ethylbenzene and the like.

Among the types of organic compounds which may be dehydrogenated by means of the process of this invention are nitriles, amines, alkyl halides, ethers, esters, aldehydes, ketones, alcohols, acids, alkyl aromatic compounds, alkyl heterocyclic compounds, cycloalkanes, alkanes, alkenes and the like.

Suitable dehydrogenation reactions are the following: acyclic compounds having 4 to 5 non-quarternary contiguous carbon atoms to the corresponding olefins, diolefins or acetylenes having the same number of carbon atoms; aliphatic hydrocarbons having 6 to 16 carbon atoms and at least one quaternary carbon atom to aromatic compounds, such as 2,4,4-trimethylpentene-1 to a mixture of xylenes; acyclic compounds having 6 to 16 carbon atoms and no quaternary carbon atoms to aromatic compounds such as n-hexenes to benzene; cycloparaffins and cycloolefins having 5 to 8 carbon atoms to the corresponding olefin, diolefin or aromatic compound, e.g., cyclohexane to cyclohexene or cyclohexadiene or benzene; aromatic compounds having 8 to 12 carbon atoms including one or two alkyl side chains of 2 to 3 carbon atoms to the corresponding aromatic with unsaturated side chain such as ethyl benzene to styrene.

Illustration of dehydrogenations include butane to butenes and butadiene; propionitrile to acrylonitrile; propionaldehyde to acrolein; ethyl chloride to vinyl chloride; methyl isobutyrate to methyl methacylate; 2 or 3-chlorobutene-1 or 2,3-dichlorobutane to chloroprene; ethyl pyridine to vinyl pyridine; ethylbenzene to styrene; isopropylbenzene to $\alpha$-methyl styrene; ethylchlorohexane to styrene; cyclohexane to benzene; ethane to ethylene to acetylene; propane to propylene or methyl acetylene or allene; isobutane to isobutylene; isopentane to isoanylene and isoprene; n-butene to butadiene-1,3 and vinyl acetylene; methyl butene to isoprene; cyclopentane to cyclopentene and cyclopentadiene; n-octane to ethyl benzene and orthoxylene; monomethylheptanes to xylenes; ethyl acetate to vinyl acetate; 2,4,4-trimethylpentane to xylenes; and the like.

The preferred compounds to be dehydrogenated are hydrocarbons with a particularly preferred class being acyclic non-quaternary hydrocarbons having 3 to 5 carbon atoms or ethyl benzene and the preferred products are propene, n-butene-1 or 2, butadiene-1,3, vinyl acetylene, 2-methyl-1-butene, 3-methyl-1-butene, 3-methyl-2-butene, isoprene, styrene or mixtures thereof. Especially preferred as feed are n-butane, isopentane, ethyl benzene mixtures thereof such as hydrocarbon mixtures containing these compounds in at least 50 mol percent.

The dehydrogenation reaction may be carried out at atmospheric pressure, superatmospheric pressure or at sub-atmospheric pressure. The total pressure of the system will normally be about atmospheric pressure or sub-atmospheric pressure. Generally the total pressure will be between about 1 p.s.i.a. and about 75 p.s.i.a. Preferably the total pressure will be less than about 50 p.s.i.a.

The temperature of the dehydrogenation reaction will generally be in a range of about 350° to 700°C with excellent results being obtained in the range of 400° to 650°C. The gaseous reactants can be conducted through the reaction chamber at a fairly wide range of flow rates. The optimum flow rates will be dependent upon such variables as the temperature of reaction, pressure, particle size of the catalyst, and so forth. Desirable flow rates may be established by one skilled in the art. Generally the flow rates will be within the range of about 0.10 to 10 liquid volumes of the organic compound to be dehydrogenated per volume of dehydrogenation zone containing catalyst per hour (referred to as LHSV). Usually the LHSV will be between 0.15 and about 5. For calculation, the volume of a fixed bed dehydrogenation zone containing the catalyst is that original void volume of reactor space containing catalyst.

The dehydrogenation is carried out in a series of cycles which comprise dehydrogenation of a suitable feed over the catalysts of the invention under the conditions as defined for a period of time, usually about 6 to 12 minutes followed by a regeneration cycle during which the coke deposited from the dehydrogenation is burnt off. The regeneration can be longer or shorter than the dehydrogenation cycle as needed to remove the coke, usually about 6 to 12 minutes will be sufficient. The coke is removed by passing oxygen at a temperature of 550° to 650° C. over the catalyst. A convenient source of oxygen is air, however, pure oxygen or a mixture of oxygen with inert gases, such as nitrogen, either in the same or different proportions as air, can be used.

The following Examples which are submitted to demonstrate the operation of the chromites prepared according to the present invention are divided into two sections relative to the reactor. In the first section, the dehydrogenation process was carried out at atmospheric pressure, i.e., about 15 p.s.i.a. In the second section, a vacuum reactor was employed. The absolute numbers of the results may vary as compared between the atmospheric and vacuum reactors; however, the trends, results, and relative differences in catalyst types are comparable. The presence of the chromite structure was established for the catalysts by X-ray analysis as described previously. In the Examples, percents are by weight except that results are given as mol percents. Analysis of the products was by gas-liquid chromatography.

Isothermal Atmospheric Reactor (EXAMPLES 1–4)

The reactor was a 29 × ¾ inch Vycor tube equipped with a heating mantle and appropriate equipment. A 40 cc bed of catalyst was placed in the reactor and reactant feed (or regenerative air) passed over it. The catalyst was heated to the reaction temperature in a nitrogen atmosphere. The process was carried out automatically with a make cycle (dehydrogenation) of 9 minutes and 9 minutes oxygen regeneration and repeat of the cycle. This gave a total cycle time of 18 minutes. When desired, the partial pressure of the n-butane during the reaction cycle was reduced below atmospheric by dilution with nitrogen. The total effluent from either or both cycles was collected in an inflatable collecting device and analyzed by gas chromatography. Alternately, the effluent from the regeneration cycle was passed through a calibrated infrared analyzer to determine the amount of $CO_2$ produced during regeneration (coke burn-off). By either method of analysis the amount of coke deposited on a catalyst during the reaction cycle was determined and could be taken into account when calculating the overall activity and selectivity of a catalyst. The temperatures were controlled by a thermoelectric temperature controller and recorded on a Leeds and Northrup recorder.

EXAMPLE 1

To 1000 ml of deionized water was added 248.8g of $CrO_3$ (Baker Analyzed Reagent, assay 99% $CrO_3$). This was stirred until dissolution was complete and 50.5g of basic magnesium oxide (Baker AR CL, assay 99.1% MgO) was then added with continued stirring. After all materials had dissolved, 450g of 37% aqueous formaldehyde solution (Celanese, uninhibited) was added. The mixture was diluted to 1750 ml total volume with deionized water. The mixture was heated to 97°–99° C and maintained at this temperature for five hours. During this period the volume of the solution was maintained at 1750 ml.

After reacting five hours, the hot mixture was filtered by suction. The filter cake was collected and the filtrate was returned to the reaction vessel.

To the filtrate from the previous reaction was added 248.8g $CrO_3$ followed by 50.5g basic magnesium carbonate (as described above). The mixture was heated with stirring (about 5 minutes) until the reagents dissolved. Then 450g of 37% aqueous formaldehyde was added with stirring. The mixture was diluted to a total volume of 2000 ml with deionized water. The mixture was heated to 97°–99°C for 5 hours and then filtered as before. The filtrate was used in this manner to prepare six individual batches of precipitate. Since these experiments were run in duplicate, this yielded 12 batches of precipitate (not including the precipitates from the first reaction.) The $Cr_2O_3$/MgO weight ratio of these 12 batches of precipitate averaged 3.8. Theoretical for stoichiometric $MgCr_2O_4$ is 3.77

The catalytic activity, when tested in an atmospheric pressure reactor at 600°C[1], of magnesium chromite from a filtrate recycle preparation $Cr_2O_3$/MgO weight ratio of 3.93 which was then calcined to 700°C in $O_2$, modified with 30 wt% aluminum sulfate and supported on AMC alumina as 45% actives, was[2] C = 67.4%, $S_{Bu}$ = 65.3%, $S_{Bd}$ = 14.6%, $Y_{Bu}$ = 44.0%, $Y_{Bd}$ = 9.8%. When tested under comparable conditions, Harshaw CrO2 11 gave: C = 68%; $S_{Bu}$ = 64%, $S_{Bd}$ = 11%, $Y_{Bu}$ = 43%, $Y_{Bd}$ = 7.5%.

[1] Feed 92% butane, 6% butylene + 1–8% isobutane
[2] mol percent, C = conversion, $S_{Bu}$ = selectivity butenes, $S_{Bd}$ = selectivity butadiene, Y = yield = C + S.

EXAMPLE 2

The procedure of Example 1 was followed except that paraformaldehyde was the reducing agent. The catalyst was calcined in $O_2$ and nitrogen. The results of dehydrogenation are given below.

| Calcining Atmosphere | C | $S_{Bu}$ | $S_{Bd}$ | $Y_{Bu}$ | $Y_{Bd}$ |
| --- | --- | --- | --- | --- | --- |
| $O_2$ | 51.4 | 67.3 | 15.9 | 34.6 | 8.2 |
| $N_2$ | 57.8 | 60.8 | 14.6 | 35.1 | 8.4 |

EXAMPLE 3 201.6 grams of $CrO_3$ (Baker AR, 99.2%) was dissolved in sufficient deionized water to make 400 ml of solution. 130.7 grams of cobalt carbonate (Baker AR, 45.1% Co) was added slowly to the vigorously stirred solution. During this addition, the mixture heated to ~60°C. 500 ml of 36–38% formaldehyde inhibited with 10–15% methanol was added and stirred for two hours; there was no reaction noted until the mixture was heated ~85°C, where a mild exothermic reaction occurred and the color of the solution changed from red-brown to blue-black. The mixture was heated to boiling for one hour then quickly filtered while hot. The black precipitate was washed with 100 ml of deionized water and dried in air then for ~36 hours at 110°C. The weight ratio of $Cr_2O_3/CoO$ was 2.46 theoretical 2.03. One portion was calcined under $N_2$ at 700° and deposited on AMC with 30% $Al_2(SO_4)_3 \cdot 16H_2O$ (aluminum sulfate). A second portion was calcined in air at 700° C and deposited on AMC alumina with 30% aluminum sulfate. The results of dehydrogenation of a feed as in Example 1 are given below.

| Calcining Atmosphere | C | $S_{Bu}$ | $S_{Bd}$ | $Y_{Bu}$ | $Y_{Bd}$ |
|---|---|---|---|---|---|
| Air | 44.7 | 56.9 | 14.3 | 25.4 | 6.4 |
| $N_2$ | 42.8 | 70.8 | 15.8 | 30.3 | 6.8 |

EXAMPLE 4

A zinc chromite was prepared by dissolving 250 grams of $CrO_3$ (Baker AR, 99.3%) 500 cc of deionized water. 140.6 grams of Zn carbonate (Baker AR, ZnO = 71.8%) was added to this solution in small portions with stirring. After all of the $ZnCO_3$ had been added, 500 grams of 37% formaldehyde was added in a single increment and the solution diluted to a total volume of 1,750 cc with demineralized water. The mixture was heated with stirring until the reaction became self-sustaining without applied external heat (after the induction period, the reaction proceeded smoothly at about 97°–99°C exothermically). When the reaction temperature dropped to 90°C, external heat was reapplied to maintain 96°–99°C temperature. The total reaction time was 4–5 hours. The resulting precipitate was suction filtered from the hot solution, dried in an oven for about 16 hours at 100°C. The material was hammer milled and samples were calcined in $N_2$ and $O_2$ at 700°C.

Isothermal Vacuum Reactor
(EXAMPLES 5–11)

The reactor was an alonized 316 SS tube, 24 inches long and 1 inch in diameter equipped with a heating mantel and thermoelectric temperature controller. A 160 cc bed of catalyst (112 cc of catalyst mixed with 48 cc of fused alumina balls) was used for each run. The reactant feed was passed down through the catalyst bed and the products removed at the bottom. The catalyst was heated to reaction temperature in a nitrogen atmosphere. The process was carried out in cycles of 9 minutes of reaction, 1 minute of nitrogen purge, 9 minutes of regeneration, followed by reaction, etc. A vacuum of 22 inches of Hg was maintained during the reaction cycle and atmosphere pressure used during nitrogen purge and regeneration cycle. Substantially the same analytical procedures were followed for the analysis of the product gases as in the atmospheric process.

EXAMPLES 5 and 6

The magnesium chromite prepared in Example 1 was employed to prepare catalysts as pellets and as extrudate which were employed in the dehydrogenations. The feed was 2.1% isobutane, 89.3% butane, and 8.6% butenes. The results are set out below in TABLE I.

TABLE I

| Reaction Cycle: | 9 min. reaction = 590 cc/min. of hcbn feed | 1 min. $N_2$ purge | 9 min. regeneration = 300 cc/min. $O_2$ + 1200 cc.min. $N_2$ |
|---|---|---|---|

| Example | Catalyst | Total Hrs. on Stream | $T_m$, C | Results, Mol % $C/S_{Bu} + S_{Bd}/Y_{Bu} + Y_{Bd}$ |
|---|---|---|---|---|
| 5 | Pellets* | 237 | 530 | 37.5/72.8+9.0/27.3+3.4 |
|   |          | 352 | 530 | 37.6/73.1+9.2/27.5+3.4 |
|   |          | 400 | 530 | 38.6/74.2+8.7/28.7+3.4 |
| 6 | Extrudates* | 337 | 535 | 38.2/72.0+11.6/27.5+4.4 |
|   |          | 481 | 535 | 40.1/72.1+11.6/28.9+4.7 |
|   |          | 625 | 535 | 39.6/72.8+11.7/28.9+4.6 |

*Diluted 70/30 with alundum

EXAMPLES 7 to 11

These Examples are submitted as a comparison between chromites used as dehydrogenation ctalyst prepared according to the invention and by prior art methods. Examples 9 and 10 are according to the present invention. The results of the dehydrogenation are in TABLE II.

TABLE II

| Reaction Cycle: | 9 min. reaction = 590 cc/min. of hcbn feed[1] | 1 min. $N_2$ purge | 9 min. regeneration = 300 cc/min. $O_2$ 30 1200 cc/min. $N_2$. |
|---|---|---|---|

| Example | Catalyst[2] | Total Hrs. on Stream | $T_m$, °C | Results, Mol % $C/S_{Bu} + S_{Bd}/Y_{Bu} + Y_{Bd}$ |
|---|---|---|---|---|
| 7 | 58.5 wt. % $MgCr_2O_4$[3a] + 31.5 wt. % $Al_2(SO_4)_3 \cdot 16H_2O$ + 10 wt. % PVA | 113 | 510 | 43.9/69.7 + 6.2/30.6 + 2.7 |
|   |   | 161 | 500 | 38.9/75.1 + 5.4/29.2 + 2.1 |
|   |   | 185 | 500 | 38.5/74.1 + 6.1/28.6 + 2.4 |
|   |   | 306 | 500 | 38.5/74.9 + 6.2/28.8 + 2.4 |

TABLE II-continued

| | 9 min. reaction = Reaction Cycle: 590 cc/min. of hcbn feed[1] | 1 min. $N_2$ purge | 9 min. regeneration = 300 cc/min. $O_2$ 30 1200 cc/min. $N_2$. | |
|---|---|---|---|---|

| Example | Catalyst[2] | Total Hrs. on Stream | $T_m$, °C | 10 Results, Mol % $C/S_{Bu} + S_{Bd}/Y_{Bu} + Y_{Bd}$ |
|---|---|---|---|---|
| 8 | 58.5 wt. % $MgCr_2O_4$[3b] + 31.5 wt. % $Al_2(SO_4)_3 \cdot 16H_2O$ + 10 wt. % PVA | 66 | 555 | 47.1/57.5 + 12.0/27.1 + 5.6 |
| | | 187 | 540 | 45.1/65.2 + 10.4/29.4 + 4.7 |
| | | 210 | 540 | 45.8/65.3 + 11.2/29.9 + 5.1 |
| | | 258 | 530 | 41.8/68.5 + 10.5/28.6 + 4.4 |
| | | 330 | 530 | 41.1/68.7 + 10.7/28.2 + 4.4 |
| 9 | 58.5 wt. % $MgCr_2O_4$[4a] + 31.5 wt. % $Al_2(SO_4)_3 \cdot 16H_2O$ + 10 wt. % PVA | 114 | 520 | 50.6/57.5 + 6.9/29.1 + 3.5 |
| | | 138 | 500 | 38.5/65.7 + 6.9/25.3 + 2.7 |
| | | 162 | 500 | 37.9/67.2 + 6.2/2/25.4 + 2.4 |
| 10 | 58.5 wt. % $MgCr_2O_4$[4b] + 31.5 wt. % $Al_2(SO_4)_3 \cdot 16H_2O$ + 10 wt. % PVA | 119 | 540 | 48.0/62.3 + 9.2/29.9 + 4.4 |
| | | 141 | 525 | 44.8/63.8 + 7.9/28.6 + 3.5 |
| | | 162 | 515 | 41.2/67.5 + 7.2/27.8 + 3.0 |
| 11 | 67.5 wt. % $MgCr_2O_4$[5] + 22.5 wt. % $Al_2(SO_4)_3 \cdot 16H_2O$ + 10 wt. % PVA | 90 | 555 | 38.1/61.1 + 13.5/23.3 + 5.1 |
| | | 114 | 560 | 39.4/58.3 + 14.8/23.0 + 5.8 |

[1]Feed = 92% n-butane + butylenes + 1.8% isobutane.
[2]Prepared into 5/32" dia. pellets.
[3]$MgCr_2O_4$ prepared by calcination of a dried slurry of hydrated Cr (III) oxide + Marinco CL basic magnesium carbonate + catalytic amount of $MgCl_2$ to 700°C in an atmosphere of (a) $N_2$ and (b) $O_2$.
[4]$MgCr_2O_4$ precursor prepared by reduction of a solution of MgO and $CrO_3$ with aqueous formaldehyde in a precedure similar to that of Example 1, with the filtrate from the first run being made up to produce the chromite precursor. The precursor was calcined to 700°C in an atmosphere of (a) $N_2$ and (b) $O_2$ to prepare the final actives of magnesium chromite.
[5]$MgCr_2O_4$ precursor prepared by coprecipitating a Cr/Mg = 2/1 chloride solution in conc. aq. ammonia. The dried coprecipitate was calcined to 850°C in $O_2$ and washed with demineralized water (pH = 10 with $NH_3$) before use in preparing the final actives of catalyst.

The invention claimed is:

1. A method for preparing metal chromites comprising preparing an aqueous solution of a chromium (VI) oxygen containing compound and a soluble compound of a divalent metal selected from the group consisting of Mg, Sr, Ba, Fe, Mn, Co, Ni, Cu, Zn, Cd and mixtures thereof, admixing a soluble organic reducing agent with said aqueous solution, heating the solution to a temperature of about 75° to 100°C., precipitating a substantially water insoluble divalent metal chromite compound of chromium (III) and said divalent metal, recovering said precipitate, and calcining said precipitate to produce an activated dehydrogenation catalyst.

2. The method according to claim 1 wherein said calcination temperature is up to 1300° C.

3. The method according to claim 2 wherein said calcination temperature is in the range of 400° to 1100°C.

4. The method according to claim 1 wherein said reducing agent is present in a stoichiometric excess of about 50 to 4000 mol % based on Cr(VI).

5. The method according to claim 1 wherein said divalent metal is Mg, Co, or Zn.

6. The method according to claim 1 wherein divalent metal is at least Mg.

7. The method according to claim 1 wherein divalent metal is at least Co.

8. The method according to claim 6 wherein said reducing agent is present in a stoichiometric excess of about 50 to 400 mol % based on Cr(VI) and said mixture thereof with said soluble compounds is at a temperature in the range of 90° to 100°C.

9. The method according to claim 8 wherein said precipitate is calcined at a temperature in the range of 400° to 1100° C. to produce an activated dehydrogenation catalyst.

10. The method according to claim 9 wherein said reducing agent is formaldehyde.

11. The method according to claim 9 wherein said reducing agent is paraformaldehyde.

12. The method according to claim 9 wherein said calcination is carried out in an atmosphere consisting essentially of oxygen.

13. The method according to claim 9 wherein said calcination is carried out in an atmosphere consisting essentially of nitrogen.

14. A method of producing a dehydrogenation catalyst comprising:
preparing an aqueous solution of a chromium (VI) oxygen containing compound, and a soluble compound of Mg which forms a Mg chromite upon reduction,
admixing a soluble organic reducing agent with said aqueous solution
maintaining a temperature in the range of 90° to 100° C.,
precipitating a soluble water insoluble Mg chromite compound of chromium (III) and Mg,
recovering said precipitate,
calcining said precipitate at a temperature in the range of 400° to 1100° C., and
admixing said calcined precipitate with aluminum oxide.

* * * * *